United States Patent [19]

Allen et al.

[11] Patent Number: 6,066,337
[45] Date of Patent: May 23, 2000

[54] METHOD FOR PRODUCING A RAPIDLY DISSOLVING DOSAGE FORM

[75] Inventors: Loyd V. Allen, Edmond; Bingnan Wang, Oklahoma City, both of Okla.; John Desmond Davies, Grosse Pointe Farms, Mich.

[73] Assignee: The Board of Regents of the University of Oklahoma and Janssen Pharmaceutica, Inc.

[21] Appl. No.: 09/111,113

[22] Filed: Jul. 6, 1998

Related U.S. Application Data

[63] Continuation-in-part of application No. 08/487,268, Jun. 7, 1995, Pat. No. 5,776,491, which is a continuation-in-part of application No. 08/191,237, Feb. 3, 1994, Pat. No. 5,807,576, which is a continuation-in-part of application No. 08/187,670, Jan. 27, 1994, Pat. No. 5,595,761.

[51] Int. Cl.[7] ............................. A61K 9/14; A61K 9/16; A61K 9/46
[52] U.S. Cl. ......................... 424/484; 424/465; 424/466; 424/489; 514/774
[58] Field of Search ................................. 424/464, 465, 424/484, 488, 489, 466

[56] References Cited

U.S. PATENT DOCUMENTS

| | | | |
|---|---|---|---|
| 4,013,784 | 3/1977 | Speiser | 424/19 |
| 4,572,832 | 2/1986 | Kigasawa et al. | 424/19 |
| 5,082,667 | 1/1992 | Van Scoik | 424/469 |
| 5,178,878 | 1/1993 | Wehling et al. | 424/466 |
| 5,215,756 | 6/1993 | Gole et al. | 424/484 |

FOREIGN PATENT DOCUMENTS

| | | |
|---|---|---|
| 2111423 | 7/1983 | United Kingdom . |
| 9310762 | 6/1993 | WIPO . |
| 9414422 | 7/1994 | WIPO . |

*Primary Examiner*—James M. Spear
*Attorney, Agent, or Firm*—Dunlap, Codding & Rogers, P.C.

[57] ABSTRACT

A particulate support matrix, and a dosage form made therefrom, and processes for making such support matrices and dosage forms, which disintegrate or dissolve in a matter of just a few seconds once placed into an aqueous environment. First, a porous particulate powder matrix which will serve as the dosage form matrix is produced. In a second step, the pharmaceutical, for example an antihistamine, decongestant, or antibiotic is combined with the powder. Other additives may also be added to the mixture. In a third step the mixture is formed into a dosage form. Finally, in a fourth step, a coating may be formed upon the outer surface of the dosage form to enhance the intactness and durability of the dosage form.

23 Claims, No Drawings

METHOD FOR PRODUCING A RAPIDLY DISSOLVING DOSAGE FORM

CROSS REFERENCE TO RELATED APPLICATIONS

The present application is a continuation-in-part of U.S. Ser. No. 08/487,268, filed Jun. 7, 1995, entitled RAPIDLY DISSOLVING DOSAGE FORM, now U.S. Pat. No. 5,776,491, issued Jul. 7, 1998, which is a continuation-in-part of U.S. Ser. No. 08/191,237, filed Feb. 3, 1994, U.S. Pat. No. 5,807,576 entitled "RAPIDLY DISSOLVING ORAL DOSAGE FORM", which is a continuation-in-part of U.S. Ser. No. 08/187,670, filed Jan. 27, 1994, now U.S. Pat. No. 5,595,761, issued on Jan. 21, 1997.

FEDERALLY SPONSORED RESEARCH OR DEVELOPMENT

Not Applicable

BACKGROUND OF THE INVENTION

The present invention relates to a particulate support matrix, to rapidly dissolving pharmaceutical dosage forms made therefrom, and to processes of preparing such a support matrix and such a dosage form.

The recent, current and projected growth of the elderly population in the U.S. and abroad is well recognized. Currently, 12% of the U.S. population is 65 years of age or older and receives nearly 30% of the medications prescribed. It is anticipated that there may be a 10% to 60% increase in the demand for drugs by the elderly under some new government programs. In spite of the disproportionately large demand for prescription pharmaceuticals among the elderly, relatively little attention has been directed to meeting the unique pharmacotherapeutic needs of this age group. Drug products are currently designed for three groups of individuals: infants, pediatrics and adults. The needs of the infants are obviously different from those of children 2 to 12 years of age and the needs of children are obviously different from those of adults. However, the needs of the elderly population are being overlooked as they have special characteristics that necessitate dosage forms designed especially for them. Many older patients have difficulty swallowing tablets or capsules and yet the vast majority of dosage forms administered to the elderly are tablets or capsules. Uncoated tablets are convenient and economical to manufacture but are often difficult to swallow and often cause discomfort by "hanging" in the throat. Coated tablets and capsules are somewhat easier to swallow but with increasing age and the large number of drug products that are administered to a single individual, this is a source of apprehension. Liquid dosage forms are relatively easy to administer but are more costly, easily spilled, often do not taste good, occupy large volumes of space per dosage unit, and possess some inherent stability problems. As is evident, the needs of the elderly differ from those of other populations and deserve special attention in new drug development, product formulation, posology, product packaging, product labeling, patient information, and product marketing and sales. A practical and new dosage form would be of value for these patients.

Pediatric patients generally have difficulty swallowing until they reach the age of about 10–16 years old. Younger pediatric patients generally take either chewable tablets, crush and mix regular tablets with food/juice, or take a liquid dosage form. Chewable tablets, generally a good dosage form, do not always taste good. Crushing and mixing regular tablets with food or juice, is time-consuming, messy and not always practical. The difficulty of liquid dosage forms, i.e., syrups, is that they are bulky, do not always taste good, and that drugs are not as stable in a liquid dosage form as they are in a solid dosage form, such as a tablet. A practical and new dosage form would also be of value for these patients.

Incarcerated patients often will retain their medications within the oral cavity while pretending to swallow them. These can then be accumulated and taken all at once for an enhanced drug effect. Obviously, this can be very dangerous. A dosage form which would not remain intact once placed in the oral cavity would be useful when treating these patients.

There are currently several fast-dissolving products on the market. These products have a number of drawbacks including the manufacturing methods used, taste masking, and pre-versus post-loading techniques that are required. One commercially available dosage form is prepared by a lyophilization, or freeze-drying, technique which is slow and expensive. Because each "batch" of material must be handled in its entirety, the tablet cannot be produced using a continuous process where raw materials come in and finished product is output at the other end. This tablet can be either pre-loaded (i.e., the drug is added to the tablet matrix before the tablet is formed) or post loaded (the drug is added after the tablet "blank" is prepared).

One difficulty with a freeze-dried dosage form is that of taste masking. To effectively mask the taste of poorly tasting drugs, it is generally necessary to micro-encapsulate or nano-encapsulate them. Then, if they are pre-loaded, the encapsulating shell material may dissolve during the tablet production process allowing the drug to leak into the tablet matrix, resulting in a poorly tasting product. If the tablet is post-loaded, the tablet may become disfigured causing the tablet to be disposed of or handled again, adding extra expense to the process.

Another commercially available dosage form is prepared using solid state dissolution techniques. These manufacturing methods are expensive and add additional cost to the tablet. This tablet must be post-loaded. This is necessary because drugs are generally soluble in the water and alcohol which is used in the preparation of the tablet. As with the freeze-dried dosage form discussed above, when a solution of the drug is post-loaded onto the matrix blank, often the tablets become disfigured. Another problem encountered with the solid state dissolution technique is the selection of a solvent material that will evaporate quickly but will not attack the microcapsule shell surrounding the active drug.

Effervescent dosage forms contain substantial percentages of compounds for enhancing tablet breakup and dissolution which may also serve to mask the taste of certain medications. These tablets depend upon approximate stoichiometric quantities of sodium bicarbonate and an acid, e.g., citric acid or tartaric acid, reacting to form $CO_2$ to break up the tablet in the mouth. The difficulty with the commercially available effervescent tablets is that the mouth tends to "foam" leaving an uncomfortable feeling to many.

BRIEF DESCRIPTION OF THE DRAWINGS

Not Applicable

SUMMARY OF THE INVENTION

According to one aspect of the invention, there is provided a particulate matrix comprising a first polymeric component having a predetermined net charge when in solution, a second polymeric (solubilizing) component having a predetermined net charge when in solution of the same sign as the net charge of the first polymeric component, and a bulking agent, characterized in that the second polymeric component has a solubility in aqueous solution greater than that of the first polymeric component.

According to another aspect of the invention, there is provided a rapidly dissolving pharmaceutical dosage form comprising: a particulate support matrix comprising a first polymeric component having a predetermined net charge when in solution, a second polymeric component having a predetermined net charge when in solution of the same sign as the net charge of the first polymeric component, and a bulking agent, and wherein the second polymeric component has a solubility in aqueous solution greater than that of the first polymeric component; and a pharmaceutical ingredient mixed with the particulate support matrix. The support matrix is generally substantially completely disintegrable within less than about 20 seconds when the dosage form is introduced into an aqueous environment so as to release the pharmaceutical ingredient to the aqueous environment.

DESCRIPTION OF THE PREFERRED EMBODIMENTS

The present invention comprises a particulate support matrix, a dosage form made therefrom which disintegrates or dissolves in a matter of just a few seconds once placed into the oral cavity, or other aqueous environment and methods for making such support matrix and dosage form. This rapidly dissolving tablet or other dosage form made from the matrix described herein has many of the characteristics of a regular tablet up to the point of administration, i.e., convenient size, stable, easy to dispense, easily transportable, easy to alter the dose and easy to administer. Upon placing this dosage form in the mouth, the saliva will serve to rapidly dissolve the dosage form and the patient in effect will swallow the medication in a liquid form. The rapid-dissolving tablets of the present invention will eliminate many of the problems inherent in the other forms of orally-disolving tablets described above since the matrix and active drug powders are blended and formed into tablets in the same way as regular tablets, except that a very light compression pressure is used in forming the tablets of the present invention.

Where used herein the term "dosage form" is meant to include any dosage form which is intended to be dissolved in any aqueous medium including water, saliva or other aqueous biological fluids or suspensions, and may include tablets, capsules, caplets, boluses, powders cachets, pills and granules.

If a drug entity has little or no taste, the dosage form will generally be prepared to be almost tasteless. If a drug product does have a characteristic, undesirable taste, the taste will preferably either be altered by different mechanisms such as flavorings to make it acceptable, or the drug will be micro- or nano-encapsulated with a coating that dissolves at an acidic pH and incorporated into the tablet. This rapid dissolving tablet will not only provide the geriatric, pediatric and incarcerated populations with an easy to use tablet, but may also result in long-term benefits such as enhanced patient compliance, fewer hospital admissions due to poor compliance, and enhanced health and quality of life.

Furthermore, the application of this dosage form is not limited to oral delivery as it is also applicable for use as a fast dissolving tablet when administered to other moist areas of orifices of the body, such as the rectum.

Generally, the method of the present invention comprises up to four steps. First, a porous particulate powder which will serve as the tablet support matrix is produced. In the second step, the pharmaceutical, for example an antihistamine, decongestant, or antibiotic is combined with the powder. Other additives may also be added to the mixture. In the third step the mixture is formed into a tablet or other dosage form. Finally, in the fourth step, a coating may be applied to the outer surface of the tablet or other dosage form or the dosage form may be otherwise treated to enhance the intactness and durability of the tablet or other dosage form.

More particularly, the invention comprises a particulate support matrix for use in forming a pharmaceutical dosage form and a process for producing it. The process comprises the steps of providing an aqueous composition which further comprises (1) an aqueous medium, (2) a support agent comprising a first polymeric component having a predetermined net charge, a second polymeric component having a predetermined net charge of the same sign as the first polymeric component, and a bulking agent and wherein the second polymeric component has a solubility in aqueous solution greater than that of the first polymeric component, and (3) a volatilizing agent for enhancing the rate of vaporization of the aqueous medium and for enhancing volume and porosity of the support agent during drying.

The particulate support matrix may optionally contain an acidifying or alkalizing agent for setting the predetermined net charge of the components of the support agent. The first polymeric component and second polymeric component of the support matrix may be provided in solution or may be provided in solid form and dissolved within the aqueous medium to form the aqueous composition along with the bulking agent. The aqueous composition is introduced as droplets into a drying chamber heated to a temperature sufficient to evaporate substantially all of the aqueous medium and volatilizing agent from the droplets. This yields the support agent as a dried and expanded particulate form comprising the particulate support matrix.

As contemplated herein, the support matrix, and the dosage form produced therefrom, may comprise more than two polymeric support components. In such a case, the more than two polymeric support components are of the same sign, and have a range of solubilities wherein one polymeric support component is less soluble than the others and another component is more soluble than the others. The most soluble polymeric component is therefore the primary polymeric solubilizing component of the present invention. It will be understood however that the other polymeric components may also contribute to the solubility of the support matrix in an aqueous environment.

The first polymeric component and the second polymeric component may have net charges which are closer to a neutral pH than is preferable for optimal rapid dissolution. For example, when the first polymeric component is an acidic gelatin, and the second polymeric component is an acidic gelatin hydrolysate, the isoelectric points may be higher than the preferred pH, which is below 5.5. In such a case, it is desired to reduce the pH of the solution to a preferred pH by the addition of an acidifying agent, such as citric acid or acetic acid. This will shift the isoelectric points of the gelatin to pH levels within the preferred range and will maintain them at such pH during the drying process.

However, when the first polymeric component and the second polymeric component have isoelectric pHs in their native form which are within the preferred pH range of about 3.5 to 5.5, it may be unnecessary to add an acidifying agent to the aqueous composition. For example, if the first and second polymeric components are polypeptides comprising a preponderance of acidic amino acids, the polypeptides may have isoelectric points which are sufficiently low. Similarly, if the polypeptides comprise a preponderance of basic amino acids, the polypeptides may have isoelectric points sufficiently basic to eliminate the need for an alkalizing agent to raise the pH of the aqueous composition.

After the net charges of the first and second polymeric components are altered (when necessary) either by an acidifying agent or by an alkalizing agent, the altered net charges will be maintained by the polymeric components due to their natural buffering capacity, The completed particulate support matrix comprises (1) a first polymeric component having a net charge when in solution, (2) a second polymeric component having a net charge when in solution of the same sign as the net charge of the first polymeric component, and (3) a bulking agent. The second polymeric component has a solubility in aqueous solution greater than that of the first polymeric component for enhancing dissolution of the particulate support matrix upon exposure to an aqueous environment. When the support matrix is introduced into an aqueous environment it is substantially completely disintegrable within less than about 20 seconds. The support matrix may be substantially completely disintegrable within less than about 10 seconds, or more preferably within from about 1 second to about 6 seconds. The particulate support matrix preferably has a bulk density within a range of about 0.03 g/ml to about 0.15 g/ml. The particulate support matrix may have a bulk density within a range of from 0.03 g/ml to about 0.3 g/ml.

The first polymeric component may comprise a first polypeptide and the second polymeric component may comprise a second polypeptide. More preferably, the first polypeptide may be a non-hydrolyzed gelatin and the second polypeptide may be a hydrolyzed gelatin. Both the first polypeptide and the second polypeptide may have a net positive charge. Alternatively, the first polypeptide and the second polypeptide may have a net negative charge. The particulate support matrix may further comprise an agent for maintaining the net charge of the first polymeric component and the second polymeric component when it is desired to maintain the net charges at pHs different from those of the pH of the native first and second components in solution.

The invention further comprises a rapidly dissolving solid pharmaceutical dosage form, which is made from an active ingredient such as a pharmaceutical product which is mixed and dispersed throughout the particulate support matrix described herein and then formed into a tablet. When this dosage form is introduced into an aqueous environment the support matrix is substantially completely disintegrable within less than about 20 seconds so as to release the pharmaceutical ingredient to the aqueous environment. The support matrix may be substantially completely disintegrable within less than about 10 seconds, or more preferably in from about 1 second to about 6 seconds. The dosage form may also contain a small amount of an effervescing agent (generally from 0 to 5% of weight and preferably less than about 3%) for aiding in the initial phase of disintegration of the dosage form, a binding agent, and a flavoring agent. Further, the dosage form may have a sintered or polymeric coating on the external surface for enhancing the intactness of the dosage form. The density of the dosage form is generally within a range of about 0.05 g/ml to about 0.4 g/ml, and is more preferably within the range of from 0.1 g/ml to about 0.2 g/ml.

Preparation of the Particulate Support Matrix

The particulate support matrix, in the preferred embodiment, is produced using standard spray-drying techniques, well known to persons of ordinary skill in the art. The components of the composition which is used to produce the matrix include a support agent which comprises in one version a non-hydrolyzed gelatin and a hydrolyzed gelatin and additionally a bulking agent for increasing the bulk and solubility of the support matrix and tablet formed therefrom. Another component is a volatilizing agent, having a volatility which exceeds that of water, such as an alcohol, preferably ethanol. Another optional component is an acidifying or alkalizing agent which functions to cause the components of the support agent to be maintained with a net charge, either positive (when the preferred pH of the composition is below neutral) or negative (when the preferred pH is above neutral). In a preferred version the support matrix is maintained with a net positive charge by an acidic agent such as citric acid. The composition further comprises an aqueous medium such as water.

Critical physical factors in the spray drying process have to do with net charge and solubility of the support agent (for example, of proteins) and the evaporation characteristics of the volatilizing agent (for example, ethanol). In the preferred embodiment, the support agent is comprised of a first polymeric component and a second (solubilizing) polymeric component and a bulking agent. The second polymeric component (solubilizing component) contributes to the support function of the support matrix when in the dried particulate but also serves to enhance the rate of dissolution of the support matrix once the tablet is introduced into an aqueous environment such as the salivary environment of the oral cavity. In one example of the preferred embodiment, the first and second components of the support agent comprise two different forms of gelatin, an unmodified gelatin (the first polymeric component), and a hydrolyzed gelatin (the second polymeric component), and act together to form a support matrix in the dried particles. Both of these forms of gelatin are commercially available. The hydrolyzed gelatin assists the unmodified gelatin as a structural component of the matrix but it also functions to increase the solubility of the matrix. In an experiment where the particulate matrix was formed only from the unmodified gelatin, water and alcohol, the powder dissolved in approximately 25 seconds. When hydrolyzed gelatin was added to the same formula, the powder produced therefrom dissolved in about 15 seconds.

In the preferred version of the invention, the solution of the protein and protein hydrolysate is made acidic, preferably in the pH range of about 3.5 to 5.5, and more preferably from about 4.0 to about 5.0. This acidity causes the protein components of the composition to have a net positive charge at a pH which enhances repulsion of the protein components. Together with or in lieu of gelatins, the first polymeric support component and/or second polymeric component may be comprised of other polymers which can maintain a net charge, including proteins, glycoproteins, acacia, alginic acid, pectin, tragacanth, and xanthan gum and which function in accordance with the present invention.

The following are examples of pairs of first polymeric support and second polymeric (solubilizing) components (respectively) (1) acacia and pectin, 2:1; and (2) tragacanth and xanthan gum, 1:3. The above ratios are approximate.

In a preferred embodiment of the invention both the first polymeric component and the second polymeric component may comprise gelatin which has been hydrolyzed wherein the first component has a molecular weight greater than that of the second component and wherein the second component has an aqueous solubility greater than that of the first component. Hydrolyzed gelatins have molecular weights ranging from 1,000 to 12,000 daltons. Furthermore, the dosage form may comprise one or more intermediate polymeric components having solubilities and molecular weights intermediate between the first polymeric component and second polymeric component contemplated herein.

The effect of the net positive charge of the protein (or polymer) molecules is to cause individual protein (or polymer) molecules to be repellent to each other when in solution thereby reducing the tendency for the protein (or polymer) molecules to "cling" to each other. As a result, the protein (or polymer) molecules tend to remain repelled in the solution and during the spray drying process while the droplets of the composition are drying into particles. As a result, the powder formed will be of relatively low bulk density, generally in the range of from about 0.03 g/ml to about 0.3 g/ml. The bulking agent contributes to the bulk and stability of the support matrix and further increases the rate at which the support matrix will dissolve. Examples of bulking agents are carbohydrates such as mannitol, sorbitol, sucrose, lactose, xylitol, and acacia. Mannitol and sorbitol are preferred bulking agents.

The incorporation of the ethanol (or another volatilizing agent) into the solvent system functions to decrease the vaporization temperature of the solvent and contributes to the production of a more porous particle having a lesser bulk density and thus a greater bulk volume. It has been discovered that if water alone is used as the aqueous solvent, when the composition is introduced as droplets into the spray drying chamber, the droplets will have a tendency to contract in size thus increasing in density, as they traverse from the spray nozzle, through the drying chamber, to the collecting chamber of the spray-drier unit. By incorporating a volatilizing agent such as ethanol into the solvent, numerous pores and channels are formed within the structure of the droplet as the solvent mixture volatilizes from the droplet during the drying process. The particle formed from the droplet retains a higher porosity and low density and even experiences expansion resulting in a powder having a larger bulk volume.

In one experiment, a control comprising a quantity of a formula excluding ethanol produced a dried particulate support matrix powder having a bulk density of 0.077 g/ml (specific bulk volume was about 13 ml/g) and a bulk volume of 180 ml. The treatment comprised a comparable initial quantity of the formula with ethanol added produced a dried particulate support matrix powder having a bulk density of 0.049 g/ml (specific bulk volume was about 20.4 ml/g) and a bulk volume of 450 ml. The formula comprised, mannitol (10 g), sorbitol (5 g), citric acid (0.4 g), sucrose (0.15 g), Explotab® (0.15 g), gelatin G8-275 (1 g), gelatin hydrolysate (1 g), and a quantity of water sufficient to produce a volume of 500 ml. The amount of ethanol added to the treatment was 150 ml.

The term "bulk volume", as used herein, is defined as the actual volume of a quantity of particulate support matrix material. The term "true volume" as used herein is defined as the volume of a quantity of particulate support matrix material after that quantity has been compacted to eliminate the void space of the quantity. The term "bulk density" as used herein is defined as the mass of a quantity of the particulate support material divided by the bulk volume of that quantity. The term "specific bulk volume" is defined as the bulk volume of a quantity of particulate support material divided by the mass of that quantity. The term "porosity" as used herein is a percentage defined as:

$$\frac{\text{bulk volume} - \text{true volume}}{\text{bulk volume}} \times 100.$$

This result of a product having a greater bulk volume when ethanol is added is apparently obtained by the lowering of the vaporization temperature of the solvent thus increasing the rate at which the solvent is vaporized. The retention of the porous nature of the particle is critical to the speed with which a tablet constructed of the material dissolves. The porosity enhances the capillary movement of saliva into the interior of the tablet thereby increasing the dissolution rate of the support matrix of the tablet.

The acidifying or alkalizing agent, when present in the composition serves to maintain the net charge of the molecules of the support matrix. For example, in one preferred embodiment, the predetermined net positive charge of the protein components is set by an acidifying agent such as citric acid. When the support matrix makes contact with an aqueous solution the proteins comprising the support matrix will have a positive charge and immediately repel each other as soon as they dissolve, thus causing the particles of the tablet to repel each other, enhancing the rapidness of disintegration of the tablet. A similar phenomenon may be effected by using an alkalizing agent such as sodium bicarbonate as an alkalizing agent (causing the polymeric components of the support matrix to be negatively charged).

In the present invention, the first polymeric and second polymeric components of the support matrix together generally comprise from 2–35% of the dry components of the aqueous composition (percentage by weight, when the composition comprises the first polymeric and second polymeric components, the bulking agent and, optionally, the buffering agent) used to form the particulate support matrix. More preferably, the range is from 5–25% and more preferably is from 10–200%. Most preferably the first polymeric and second polymeric components of the support matrix together comprise from 12–16% of dry portion of the aqueous composition. Generally, the first polymeric component and the second polymeric components are present in the formulation in a range of first polymeric component:second polymeric component ratios of from about 20:1 to about 1:100 by weight, or in a range of from about 5:1 to about 1:40, or more preferably in a range of from about 2:1 to about 1:25, or still more preferably in a range of from about 1:2 to about 1:10.

In addition, the bulking agent of the support matrix generally comprises from 45–97% of the dry components of the aqueous composition (percentage by weight) used to form the particulate support matrix. More preferably, the range is from 70–92% and more preferably is from 75–90%. Most preferably the bulking agent of the support matrix comprises from 80–85% of the dry portion of the aqueous composition. In addition, the acidifying or alkalizing agent of the support matrix generally comprises from 0–30% of the dry components of the aqueous composition (percentage by weight) used to form the particulate support matrix. More preferably, the range is from 1–16% and more preferably is from 1–6%. Most preferably, when present, the acidifying or alkalizing agent of the support matrix comprises from 1–3% of the dry portion of the aqueous composition. As noted below, the matrix may further comprise a flavoring agent preferably added during the formation of the matrix. The flavoring agent may comprise from 0% to 10% of the aqueous composition in a preferred version and more preferably from 0.001% to 0.05%.

Formation of the Tablet

Before forming the particulate support matrix into a tablet, a quantity of the drug, medication, or pharmaceutical and any desired flavoring agent is added to a quantity of the particulate support matrix. The optional addition of a small amount of effervescent material serves to assist in the initial stage of the disintegration of the particles of the tablet. The tablet may be formed by methods known to those of ordinary skill in the art. For example, the tablet may be formed by direct compression. Or, it may be formed by first adding a moistening agent such as alcohol, then compressing or molding the composition. Or, it may be formed by first adding a binding agent such as polyvinylpyrrolidone, then compressing or molding the composition into a tablet. The dosage form described herein may include one or more adjuvants which can be chosen from those known in the art including flavors, diluents, colors, binders, fillers, compaction vehicles, effervescent agents, and non-effervescent disintegrants, such as those disclosed in U.S. Pat. No. 5,178,878, issued to Wheling et al. on Jan. 12, 1993, and in U.S. Pat. No. 5,215,756, issued to Gole et al., on Jun. 1, 1993, the specifications of which are hereby incorporated herein by reference. More specifically, the tablets may be composed of, but not limited to, the following: gelatin (commercially available Pharmagel® A and B, Type A, 275 Bloom, and Type B, 100 Bloom), hydrolyzed gelatin, sugars (mannitol, sucrose), organic acids (citric acid, succinic acid), sodium bicarbonate, ethyl alcohol, disintegrants such as Explotab® (sodium starch glycollate) and AcDiSol® (modified cellulose gum), starch, polyvinylpyrrolidone polymers, alginic acid, bulking and electrical charge agents such as acacia, and polyethylene glycol polymers.

Following the formation of the mixture into a tablet, it may be desired to form a coating on or to apply a very thin coating to the external surface of the tablet. The function of the coating, when applied, is to enhance the intactness of the tablet. Due to the porous nature of the tablet, the tablet tends to be rather fragile and breakable and generally benefits from the added protection afforded by the coating. The coating may comprise a polymer, such a polyvinyl alcohol or a polyvinylpyrrolidone, which, when applied forms a polymeric "net" over and into the tablet. This "net" maintains the tablet intact but does not inhibit the capillary uptake by the tablet once placed in the aqueous environment of the oral cavity although dissolution time may be slightly increased when a coating is applied to the tablet (see Example 17).

Alternatively, a coating may be formed on the surface of the tablet or dosage form by a sintering process. Methods of sintering pharmaceutical dosage forms are well known to those of ordinary skill in the art, and one is directed to pages 87–101 in the "Encyclopedia of Pharmaceutical Technology, Vol. 14, 1996, (which is hereby incorporated herein by reference) for a review of this technology.

In a preferred version of the sintering technique used in the present invention, one or more PEGs preferably having MWs of 3000–6000, for example, PEG 3350, are pulverized to a fine powder. A quantity of this PEG powder (which may include one or more types of PEG) is mixed with the drug/support matrix mixture defined elsewhere herein. A loose tablet or dosage form is formed and heated briefly, for example at 90° C. for about 10 minutes. The PEG within the mixture melts, forming a thin coating on the tablet. No organic solvents are necessary in this sintering process. Examples of the sintering method are shown in Examples 36 and 37. One of ordinary skill in the art will be aware of other methods of forming tablet coatings.

In preparation for forming the tablets, a tablet blend is produced by combining a quantity of the particulate support matrix with a quantity of the pharmaceutical or drug and optionally with a quantity of an effervescent blend, a binding solution and/or a flavoring (or the flavoring may be added during the formation of the matrix to produce a flavored matrix).

The pharmaceutical composition can be added at several different stages of the formulation of the dosage form depending on the circumstances. The pharmaceutical can be added directly to the liquid composition before or during the spray drying process at the inlet nozzle. The resulting product can then be incorporated into the tablets. Alternatively, the pharmaceutical, in untreated or encapsulated form, is mixed with the particulate support matrix (after the spray drying process, before or after adding the binder, if a binder is added) and then formed into tablets. Alternatively, the pharmaceutical could be added by direct application to the preformed tablet by spray coating or drop coating.

As noted, the addition of the effervescent blend, the binding solution (also referred to herein as the binding agent) and the flavoring are optional. In one embodiment, the binding solution and the effervescent blend may be added to the support matrix powder in a ratio of about 20:10:1 (support matrix:binding solution: effervescent blend). The binding agent in one embodiment comprises from 0% to about 20% of the dry components of the aqueous composition and from 0% to 5% of the aqueous composition. The effervescent blend preferably consists of an approximately stoichiometric ratio of citric/tartaric acids with sodium bicarbonate in a powder form. In various versions, the effervescent blend may comprise the following ratios of components:

(1) citric acid:sodium bicarbonate, 1:1.2
(2) tartaric acid:sodium bicarbonate, 2:2.24
(3) citric acid:tartaric acid:sodium bicarbonate, 1:2:3.4

The blend is slightly acidic so there will be a slight tartness in the mouth upon dissolution of the product. As is indicated above, the amount of effervescent blend present is minimal (from 0 to 5% of total weight) such that its fizzing properties are almost non-detectable in the mouth. Its presence enhances the separation of the porous particles and enhances capillarity during dissolution of the tablet within the oral cavity thereby decreasing dissolution time of the tablet (see Example 15). The effervescent blend also enhances salivation in the oral cavity.

The binding solution in one version of the invention consists of 1% PVP-40 in ethanol (e.g., see Example 14). Other binding solutions may consist of mixtures of PEG 1000 and PEG 4000 in alcohol, or PEG 1000 and PVP 1000 in alcohol. Acetone may be substituted for ethanol or other alcohols in these formulations. The binding solution may further comprise a quantity of a surface active agent such as sodium lauryl sulfate for further increasing the dissolution rate of the dosage form. The binding solution, when used is generally incorporated by slowly mixing the solution with the spray dried powder, then drying at about 40–50° C.

In one method used for forming the tablets, a quantity of the tablet blend is lightly compressed. The tablets thus produced may be coated with a very thin coating of an organic solution of a polymer, which rapidly evaporates leaving a polymeric "net" on the surface of the tablet. This thin external "net" aids in keeping the tablets intact during handling. Polymers may include, but are not limited to PVP and PVA. The coating may be applied by passing the tablet into a chamber having a saturated atmosphere of the coating material. Alternatively, the coating may be applied by lightly spraying the coating material onto the surface of the tablet.

In another method for forming the tablets, a quantity of the tablet blend is moistened with ethanol then passed through a #40 mesh screen and immediately compressed into tablets and dried overnight at about 50° C. The tablets thus produced may be then coated with a very thin coating of an organic solution of a polymer, which rapidly evaporates leaving a "net" on the surface of the tablet. Alternatively, as discussed elsewhere herein, the coating may be formed by sintering the tablet.

The present invention contemplates a tablet which is much lighter (for example 50 mg) than a comparable typical commercially available tablet (for example 400–500 mg).

The present invention further contemplates a tablet which will disintegrate within the oral cavity in less than about 20 seconds. More preferably, the tablet will disintegrate within less than about 10 seconds. More preferably, the tablet will disintegrate within the oral cavity in less than about 6 seconds. Still more preferably, the tablet will disintegrate in from about 1 second to about 4 seconds. The bulk density of the formed tablet is preferably in a range of from about 0.1 g/ml to about 0.2 g/ml, but may be either less or greater than the bounds of this range, for example, 0.05 g/ml to 0.4 g/ml. Porosity may be in a range of from about 50 to 75% in a preferred embodiment.

EXAMPLES

The following examples further illustrate compositions of the dosage form of the present invention including preferred versions and methods of making the same; however these examples are not to be construed as limitations of this invention.

Standardized Dissolution Testing method

The testing method used to determine the dissolution of the tablet material is a modification of the USP disintegration method which involves the agitation of tablets in purified water at 37° C. The present testing conditions used a 600 ml glass beaker with water at about 37° C. The surface of the water was motionless. The water was not agitated. A fresh beaker of water was used for each test. To test the dissolution rate of the particulate matrix in powder form, the tip of a 4" stainless steel spatula was dipped into the powder and a quantity of powder equivalent to approximately 100 mg was removed from the container and dropped onto the surface of the water from a distance of approximately 2.5 cm (1 inch). To test the dissolution rate of the support matrix in tablet form, a tablet was removed from its container and placed on the tip of a 4" stainless steel spatula. The tip of the spatula was held approximately 2.5 cm (1 inch) above the surface of the water and the tablet allowed to slide off the spatula tip onto the water. The testing method is an approximation of the in vitro use of the tablet. In actual practice, of course, the tablet will be placed on the tongue and a combination of the saliva dissolving the tablet and the tongue action aiding in its breakup will occur.

Where used herein, the term "substantially completely disintegrable" means that the dosage form is dissolved in solution such that it is virtually entirely dispersed into the solution. This does not necessarily imply total disintegration or dispersion. Disintegration time is the time from immersion for substantially complete dispersion of the tablet as determined by visual observation. As used herein, the term "substantially completely disintegrable" does not require dissolution or disintegration of all microcapsules or other discrete inclusions of the dosage form, for some of these may be more slowly soluble than the particulate matrix which comprises the critical dissolution enhancing component of the dosage form.

Example 1

The following components were added to a quantity of purified water sufficient to produce a mixture with a volume of 500 ml and a pH of 2.8:

| | |
|---|---|
| Mannitol | 30.0 g |
| Gelatin G8-275 | 1.2 g |
| Gelatin Hydrolysate | 1.2 g |
| Explotab ® (Sodium Starch Glycolate, NF) | 0.6 g |
| Acacia | 0.6 g |
| PVP-10 | 0.3 g |
| Citric Acid | 1.5 g |
| Tartaric Acid | 1.5 g |
| Ethanol | 150 ml |

The mixture was introduced into a Buchi model 190 spray drier with a heat setting of 10, an aspirator setting of 5, a flow rate setting of 4.27, an initial flow control setting of 700 (changing to 650 after the first time interval), and a vacuum setting of −20. Chamber temperatures were measured at approximately 5 minute consecutive intervals during the drying process. The temperatures at the flow inlet point were 156° C., 156° C., 159° C., 154° C. and 157° C. The temperatures at the flow outlet point (the point where the dried product exits the drying chamber to product collector) were measured as 115° C., 111° C., 86° C., 109° C., and 108° C. The particulate support matrix product had a bulk volume of about 140 ml, a specific bulk volume of 5.6 ml/g and a porosity of 59.6%. The resulting matrix had a dissolution time of from 5 to 15 seconds.

Example 2

The following components were added to a quantity of purified water sufficient to produce a mixture with a volume of 500 ml and a pH of 6.4:

| | |
|---|---|
| Sucrose | 30.0 g |
| Gelatin G8-275 | 0.9 g |
| Gelatin Hydrolysate | 0.9 g |
| Explotab ® | 0.5 g |
| Ethanol | 150 ml |

The mixture was introduced into a Buchi model 190 spray drier with a heat setting of 10, an aspirator setting of 5 (which was changed to 7 after the second time interval), a flow rate setting of 4.27, a flow control setting of 700, and a vacuum setting of −20. Chamber temperatures were measured at approximately 5 minute consecutive intervals during the drying process. The temperatures at the flow inlet point were 154° C., 154° C., 133° C., 143° C., and 143° C. The temperatures at the flow outlet point (the point where the dried product exits the drying chamber to product collector) were measured as 104° C., 104° C., 90° C., 93° C., 93° C., and 93° C. The particulate support matrix product had a bulk volume of about 100 ml, a specific bulk volume of 2.3 ml/g and a porosity of 8.8%. Dissolution time of the support matrix was 5–15 seconds.

Example 3

The following components were added to a quantity of purified water sufficient to produce a mixture with a volume of 400 ml and a pH of 8.4:

| | |
|---|---|
| Mannitol | 60 g |
| Gelatin G8-275 | 1.2 g |
| Gelatin Hydrolysate | 1.2 g |
| Acacia | 0.4 g |
| Explotab ® | 0.4 g |
| Alginic Acid | 0.4 g |
| PVP-40 | 0.6 g |
| Sodium Bicarbonate | 2.4 g |
| Ethanol | 120 ml |

The mixture was introduced into a Buchi model 190 spray drier with a heat setting of 10, an aspirator setting of 5, a flow rate setting of 4.27, an initial flow control setting of 700 (changing to 550 after the first time interval), and a vacuum setting of −20. Chamber temperatures were measured at approximately 5 minute consecutive intervals during the drying process. The temperatures at the flow inlet point were 154° C., 157° C., 157° C., 157° C., and 157° C. The temperatures at the flow outlet point (the point where the dried product exits the drying chamber to product collector) were measured as 107° C., 108° C., 108° C., 108° C., and 108C. The particulate support matrix product had a bulk volume of about 60 ml, a specific bulk volume of 3.7 ml/g and a porosity of 38.8%. Dissolution time of the matrix was about 5 seconds.

Example 4

The following components were added to a quantity of purified water sufficient to produce a mixture with a volume of 400 ml and a pH of 3.0:

| | |
|---|---|
| Mannitol | 60 g |
| Gelatin G8-275 | 1.2 g |
| Gelatin Hydrolysate | 1.2 g |
| Acacia | 0.8 g |
| Explotab ® | 0.4 g |
| PVP-40 | 0.6 g |
| Citric Acid | 0.9 g |
| Tartaric Acid | 0.9 g |
| Ethanol | 120 ml |

The mixture was introduced into a Buchi model 190 spray drier with a heat setting of 10, an aspirator setting of 5, a flow rate setting of 4.27, an initial flow control setting of 700 (changing to 600 after the first time interval and to 550 after the second time interval), and a vacuum setting of −20. Chamber temperatures were measured at approximately 5 minute consecutive intervals during the drying process. The temperatures at the flow inlet point were 155° C., 150° C. and 155° C. The temperatures at the flow outlet point (the point where the dried product exits the drying chamber to product collector) were measured as 114° C., 109° C. and 108° C. The particulate support matrix product had a bulk volume of about 70 ml, a specific bulk volume of 5.11 ml/g and a porosity of 55.7%. Dissolution time of the support matrix was from 2–10 seconds.

Example 5

The following components were added to a quantity of purified water sufficient to produce an acidic mixture "Part A" with a volume of 100 ml:

| | |
|---|---|
| Mannitol | 20.0 g |
| PVP-10,000 | 1.1 g |
| Citric Acid | 3.8 g |
| Ethanol | 20.0 ml |

The following components were added to a quantity of purified water to produce a basic mixture "Part B" with a volume of 100 ml:

| | |
|---|---|
| Mannitol | 20.0 g |
| PVP-10,000 | 1.1 g |
| Sodium Bicarbonate | 5.0 g |
| Ethanol | 20.0 ml |

The two mixtures were mixed as introduced into a Buchi model 190 spray drier with the heat settings shown below, aspirator settings shown below, a flow rate setting of 4.27, a flow control setting of 700, and a vacuum setting of −20, as shown below. Chamber temperatures were measured at approximately 5 minute consecutive intervals during the drying process. These temperatures are shown as inlet and outlet readings below. The particulate support matrix product had a bulk volume of about 50 ml and a porosity of 31.2%.

| Heating | 10 | 11 | 12 | 10 | 12 | 12 | 15 | 14 |
|---|---|---|---|---|---|---|---|---|
| Inlet, ° C. | 49 | 72 | 90 | 87 | 104 | 102 | 107 | 108 |
| ° F. | 121 | 162 | 194 | 188 | 220 | 215 | 225 | 226 |
| Outlet, ° C. | 36 | 37 | 37 | 37 | 39 | 40 | 41 | 41 |
| ° F. | 96 | 98 | 98 | 98 | 102 | 104 | 106 | 106 |
| Aspirator | 6 | 6 | 6 | 6 | 15 | 15 | 20 | 20 |

Example 6

The following components were added to a quantity of purified water sufficient to produce an acidic mixture "Part A" with a volume of 100 ml

| | |
|---|---|
| Mannitol | 22.5 g |
| Gelatin 275 | 0.46 g |
| Citric Acid | 3.8 g |
| Ethanol | 30.0 ml |

The following components were added to a quantity of purified water to produce a basic mixture "Part B" with a volume of 200 ml:

| | |
|---|---|
| Mannitol | 22.5 g |
| Gelatin 275 | 0.46 g |
| Sodium Bicarbonate | 5.0 g |
| Ethanol | 30.0 ml |

The mixture was introduced into a Buchi model 190 spray drier with heat settings shown below, aspirator settings shown below, a flow rate setting of 4.27, a flow control setting of 700, and a vacuum setting of −30. Chamber temperatures were measured at approximately 5 minute consecutive intervals during the drying process. The temperatures at the flow inlet point and outlet point are shown below. The particulate support matrix product had a bulk volume of about 70 ml and a porosity of 35.9% and a dissolution time of from 6–10 seconds.

| Heating | 5 | 6 | 9 | 10 | 11 | 12 |
|---|---|---|---|---|---|---|
| Inlet, ° C. | 33 | 34 | 38 | 66 | 66 | 79 |
| ° F. | 92 | 94 | 100 | 150 | 150 | 175 |
| Outlet, ° C. | 22 | 24 | 28 | 47 | 48 | 42 |
| ° F. | 71 | 76 | 83 | 117 | 118 | 108 |
| Aspirator | 5 | 6 | 10 | 12 | 10 | 12 |

Example 7

The following components were added to a quantity of purified water sufficient to produce a mixture with a volume of 300 ml and a pH of 3.0:

| | |
|---|---|
| Mannitol | 30.0 g |
| Gelatin G8-275 | 0.9 g |
| Gelatin Hydrolysate | 0.9 g |
| Explotab ® | 0.6 g |
| Tartaric Acid | 1.8 g |
| Ethanol | 90 ml |

The mixture was introduced into a Buchi model 190 spray drier with a heat setting of 10, an aspirator setting of 5, a flow rate setting of 4.27, an initial flow control setting of 700 (changing to 650 after the first time interval), and a vacuum setting of −20. Chamber temperatures were measured at approximately 5 minute consecutive intervals during the drying process. The temperatures at the flow inlet point were 156° C., 156° C., 156° C., 156° C., and 155° C. The temperatures at the flow outlet point (the point where the dried product exits the drying chamber to product collector) were measured as 114° C., 108° C., 92° C., 89° C., and 84° C. The particulate support matrix product had a bulk volume of about 150 ml, a specific bulk volume of about 6.3 ml/g and a porosity of 64.0%. Dissolution time of the support matrix was about 5–15 seconds.

Example 8

The following components were added to a quantity of purified water sufficient to produce a mixture with a volume of 500 ml and a pH of 8.7:

| | |
|---|---|
| Mannitol | 30 g |
| Gelatin G8-275 | 1.2 g |
| Gelatin Hydrolysate | 1.2 g |
| Acacia | 0.6 g |
| Explotab ® | 0.6 g |
| PVP-40 | 0.3 g |
| Sodium Bicarbonate | 3.0 g |
| Ethanol | 150 ml |

The mixture was introduced into a Buchi model 190 spray drier with a heat setting of 10, an aspirator setting of 5, a flow rate setting of 4.27, an initial flow control setting of 700 (changing to 650 after the first time interval), and a vacuum setting of −20. Chamber temperatures were measured at approximately 5 minute consecutive intervals during the drying process. The temperatures at the flow inlet point were 160° C., 157° C., 157° C., 156° C., and 155° C. The temperatures at the flow outlet point (the point where the dried product exits the drying chamber to product collector) were measured as 115° C., 108° C., 107° C., 108° C., and 108° C. The particulate support matrix product had a relatively small bulk volume of 70 ml, a specific bulk volume of about 3.9 ml/g and a porosity of 41.5%. Dissolution time was about 5–20 seconds.

Example 9

The following components were added to a quantity of purified water sufficient to produce a mixture with a volume of 500 ml and a pH of 3.5:

| | |
|---|---|
| Mannitol | 30 g |
| Gelatin G8-275 | 0.9 g |
| Gelatin Hydrolysate | 0.9 g |
| Explotab ® | 0.6 g |
| Sucrose | 1.5 g |
| Citric Acid | 0.45 g |
| Ethanol | 150 ml |

The mixture was introduced into a Buchi model 190 spray drier with a heat setting of 10, an aspirator setting of 7, a flow rate setting of 4.27, an initial flow control setting of 700 (changing to 670 after the third time interval), and a vacuum setting of −20. Chamber temperatures were measured at approximately 5 minute consecutive intervals during the drying process. The temperatures at the flow inlet point were 156° C., 155° C., 156° C., 155° C., and 155° C. The temperatures at the flow outlet point (the point where the dried product exits the drying chamber to product collector) were measured as 117° C., 113° C., 106° C., 108° C., and 107° C. The particulate support matrix product had a bulk volume of about 175 ml with a specific bulk volume of 6.6 ml/g and a porosity of 65.6%. Dissolution time was 3–4 seconds.

Example 10

The following components were added to a quantity of purified water sufficient to produce a mixture with a volume of 1000 ml and a pH of 4.5:

| | |
|---|---|
| Mannitol | 16.0 g |
| Gelatin G8-275 | 2.0 g |
| Gelatin Hydrolysate | 2.0 g |
| Explotab ® | 0.6 g |
| PVP-40 | 0.16 g |
| Sucrose | 0.41 g |
| Citric Acid | 0.33 g |
| Ethanol | 300 ml |

The mixture was introduced into a Buchi model 190 spray drier with a heat setting of 9, an aspirator setting of 6 (changing to 7 after the first time interval), a flow rate setting of 5, an initial flow control setting of 700 (changing to 600 after the first time interval and to 500 after the fourth time interval), and a vacuum setting of −20. Chamber temperatures were measured at approximately 5 minute consecutive intervals during the drying process. The temperatures at the flow inlet point were 139° C., 143° C., 144° C., 144° C., and 142° C. The temperatures at the flow outlet point (the point where the dried product exits the drying chamber to product collector) were measured as 102° C., 94° C., 97° C., 104° C., and 94° C. The particulate support matrix product had a bulk volume of about 150 ml, a specific bulk volume of 8.7 ml/g and a porosity of 73.9%. Dissolution time was about 5–15 seconds.

Example 11

The following components were added to a quantity of purified water sufficient to produce a mixture with a volume of 500 ml and a pH of 4.3:

| | |
|---|---|
| Mannitol | 15 g |
| Gelatin G8-275 | 1.0 g |
| Gelatin Hydrolysate | 1.0 g |
| Explotab ® | 0.6 g |
| Ac Di Sol ® (Modified Cellulose Gum, NF) | 0.3 g |
| Sucrose | 0.3 g |
| Citric Acid | 0.3 g |
| Ethanol | 150 ml |

The mixture was introduced into a Buchi model 190 spray drier with a heat setting of 9, an aspirator setting of 6, a flow rate setting of 5, a flow control setting of 620, and a vacuum setting of –20. Chamber temperatures were measured at approximately 5 minute consecutive intervals during the drying process. The temperatures at the flow inlet point were 148° C., 147° C., 147° C., 147° C., and 147° C. The temperatures at the flow outlet point (the point where the dried product exits the drying chamber to product collector) were measured as 116° C., 105° C., 103° C., 102° C., and 102° C. The particulate support matrix product had a bulk volume of about 100 ml, a specific bulk volume of about 7.5 ml/g and a porosity of 69.8%. Dissolution time was 5–10 seconds.

Example 12

The following components were added to a quantity of purified water sufficient to produce a mixture with a volume of 500 ml and a pH of 4.10:

| | |
|---|---|
| Sucrose | 15.0 g |
| Gelatin G8-275 | 1.0 g |
| Gelatin Hyarolysate | 1.0 g |
| Citric Acid | 0.3 g |
| Explotab ® | 0.58 g |
| Ethanol | 150 ml |

The mixture was introduced into a Buchi model 190 spray drier with a heat setting of 9, an aspirator setting of 6, a flow rate setting of 5, an initial flow control setting of 700 (changing to 650 after the second time interval), and a vacuum setting of –20. Chamber temperatures were measured at approximately 5 minute consecutive intervals during the drying process. The temperatures at the flow inlet point were 154° C., 148° C., 145° C., 145° C., 145° C. and 147° C. The temperatures at the flow outlet point (the point where the dried product exits the drying chamber to product collector) were measured as 104° C., 104° C., 98° C., 95° C., 95° C. and 98° C. The very hygroscopic particulate support matrix product having a bulk volume of about 100 ml, a specific bulk volume of about 4.05 ml/g and a porosity of 44.1% was obtained. Dissolution time was 5–15 seconds.

Example 13

The following components were added to a quantity of purified water sufficient to produce a mixture with a volume of 500 ml and a pH of 4.0:

| | |
|---|---|
| Sorbitol | 15.0 g |
| Mannitol | 15.0 g |
| Gelatin G8-275 | 1.0 g |
| Gelatin Hydrolysate | 1.0 g |
| Explotab ® | 0.6 g |
| Citric Acid | 0.34 g |
| Ethanol | 150 ml |

The mixture was introduced into a Buchi model 190 spray drier with a heat setting of 8, an aspirator setting of 6, a flow rate setting of 5, an initial flow control setting of 700 (changing to 600 after the first time interval), and a vacuum setting of –20.

Chamber temperatures were measured at approximately 5 minute consecutive intervals during the drying process. The temperatures at the flow inlet point were 131° C., 131° C., 131° C., 131° C., 131° C. and 131° C. The temperatures at the flow outlet point (the point where the dried product exits the drying chamber to product collector) were measured as 94° C., 94° C., 94° C., 95° C. and 95° C. A granular particulate support matrix product having a bulk volume of about 250 ml, a specific bulk volume of about 6.8 ml/g and a porosity of 66.5% was obtained. Dissolution time was about 2–3 seconds.

Example 14

The following components were added to a quantity of purified water sufficient to produce a mixture with a volume of 1000 ml and a pH of 4.5:

| | |
|---|---|
| Mannitol | 15.0 g |
| Sorbitol | 15.0 g |
| Gelatin G8-275 | 2.0 g |
| Gelatin Hydrolysate | 2.0 g |
| Explotab ® | 0.8 g |
| Citric Acid | 0.7 g |
| PVP-40 | 0.3 g |
| Sucrose | 0.6 g |
| Ethanol | 300 ml |

The mixture was introduced into a Buchi model 190 spray drier with a heat setting of 8, changing to 8.5 after the second time interval, an aspirator setting of 6, a flow rate setting of 5, a flow control setting of 700, and a vacuum setting of –20. Chamber temperatures were measured at approximately 5 minute consecutive intervals during the drying process. The temperatures at the flow inlet point were 139° C., 131° C., 141° C., 138° C., 137° C., 136 ° C. and 137° C. The temperatures at the flow outlet point (the point where the dried product exits the drying chamber to product collector) were measured as 96° C., 89° C., 93° C., 92° C., 93° C., 93° C. and 93° C. The particulate support matrix product had a bulk volume of about 300 ml, a specific bulk volume of about 12.7 ml/g and a porosity of 82.1%. Dissolution time was 1–5 seconds. When a binding agent (PVP-40, 0.3 g) was added to a particulate matrix produced from this mixture, the dissolution time was 2–5 seconds in tablet form.

Example 15

The following components were added to a quantity of purified water sufficient to produce a mixture with a volume of 1000 ml and a pH of 4.0:

| | | |
|---|---|---|
| Mannitol | 18.0 g | |
| Sorbitol | 12.0 g | |
| Gelatin G8-275 | 2.0 g | |
| Gelatin Hydrolysate | 2.0 g | |
| Citric Acid | 0.73 g | |
| Ethanol | 300 ml | |

The mixture was introduced into a Buchi model 190 spray drier with a heat setting of 8.8 which increased to 9.0 after the third time interval, an aspirator setting of 2 which changed to 3 after the second time interval, a flow rate setting of 5, a flow control setting of 700, and a vacuum setting of −20. Chamber temperatures were measured at approximately 5 minute consecutive intervals during the drying process. The temperatures at the flow inlet point were 141° C., 137° C., 144° C., 144° C. and 145° C. The temperatures at the flow outlet point (the point where the dried product exits the drying chamber to product collector) were measured as 107° C., 94° C., 96° C., 97° C., 99° C., and 92° C. The particulate support matrix product had a bulk volume of about 275 ml, a specific bulk volume of about 21 ml/g and a porosity of 91.1%. Dissolution time was 1–5 seconds. A tablet produced from this matrix dissolved in about 3–5 seconds. When a quantity of an effervescent agent was added to the matrix prior to forming the tablet, the dissolution time was reduced to 15 seconds.

Example 16

The following components were added to a quantity of purified water sufficient to produce a mixture with a volume of 1000 ml and a pH of 4.10:

| | |
|---|---|
| Mannitol | 21.0 g |
| Sorbitol | 9.0 g |
| Gelatin G8-275 | 2.0 g |
| Gelatin Hydrolysate | 2.0 g |
| Citric Acid | 0.75 g |
| Sucrose | 1.5 g |
| Ethanol | 300 ml |

The mixture was introduced into a Buchi model 190 spray drier with a heat setting of 8.9, an aspirator setting of 2 which changed to 1 after the third time interval, a flow rate setting of 5, a flow control setting of 600, and a vacuum setting of −20 which changed to −15 after the second time interval. Chamber temperatures were measured at approximately 5 minute consecutive intervals during the drying process. The temperatures at the flow inlet point were 143° C., 144° C., 145° C., 145° C., 145° C. and 145° C. The temperatures at the flow outlet point (the point where the dried product exits the drying chamber to product collector) were measured as 96° C., 95° C., 94° C., 94° C., 94° C. and 94° C. The particulate support matrix product had a coarse texture and a bulk volume of about 200 ml, a specific bulk volume of about 20.5 ml/g and a porosity of 89.1%. Dissolution time was 2–3 seconds.

Example 17

The following components were added to a quantity of purified water sufficient to produce a mixture with a volume of 1000 ml and a pH of 4.0:

| | |
|---|---|
| Mannitol | 21.0 g |
| Sorbitol | 9.0 g |
| Gelatin G8-275 | 2.0 g |
| Gelatin Hydrolysate | 2.0 g |
| Citric Acid | 0.76 g |
| Explotab ® | 0.6 g |
| Ethanol | 300 ml |

The mixture was introduced into a Buchi model 190 spray drier with a heat setting of 8.9, an aspirator setting of 2 which was changed to 1 after the second time interval, a flow rate setting of 5, an initial flow control setting of 700 (changing to 650 after the second time interval), and a vacuum setting of −20. Chamber temperatures were measured at approximately 5 minute consecutive intervals during the drying process. The temperatures at the flow inlet point were 141° C., 145° C., 143° C., 144° C., 144° C. and 144° C. The temperatures at the flow outlet point (the point where the dried product exits the drying chamber to product collector) were measured as 92° C., 93° C., 91° C., 87° C., 87° C. and 87° C. The particulate support matrix product had a bulk volume of about 300 ml, a specific bulk volume of about 23 ml/g and a porosity of 89.8%. Dissolution time was about 2–3 seconds. A tablet formed from this mixture (except for Explotab®) had a dissolution time of from 1–5 seconds. When the tablet was coated with 0.5% PVP-10 in chloroform, dissolution time was 2–5 seconds.

Example 18

The following components were added to a quantity of purified water sufficient to produce a mixture with a volume of 1000 ml and a pH of 4.2:

| | |
|---|---|
| Mannitol | 30.0 g |
| Gelatin G8-275 | 2.0 g |
| Gelatin Hydrolysate | 2.0 g |
| Citric Acid | 0.46 g |
| Sucrose | 0.56 g |
| Explotab ® | 0.6 g |
| Ethanol | 300 ml |

The mixture was introduced into a Buchi model 190 spray drier with a heat setting of 8.9, an aspirator setting of 1, a flow rate setting of 5, a flow control setting of 650, and a vacuum setting of −15. Chamber temperatures were measured at approximately 5 minute consecutive intervals during the drying process. The temperatures at the flow inlet point were 152° C., 142° C., 145° C., and 145° C. The temperatures at the flow outlet point (the point where the dried product exits the drying chamber to product collector) were measured as 90° C., 81° C., 86° C., and 87° C. A particulate support matrix product having a rather small bulk volume of about 150 ml, a specific bulk volume of about 15 ml/g and a porosity of 85.5% was obtained. Dissolution time was about 5 seconds.

Example 19

In a particularly preferred composition, the following components were added to a quantity of purified water sufficient to produce a mixture with a volume of 1000 ml and a pH of 4.2:

| | | |
|---|---|---|
| Gelatin G8-275 | 1.0 g | |
| Gelatin Hydrolysate | 3.0 g | |
| Mannitol | 20.0 g | |
| Xylitol | 5.0 g | |
| Sorbitol | 5.0 g | |
| Sucrose | .68 g | |
| Citric Acid | 1.0 g | |
| Propylene Glycol | 10 drops | |
| Acetic Acid, Glacial | 6 drops | |
| Ethanol | 300 ml | |

After spray drying this product produces approximately 300 mL. To produce a tablet, the above powder may be placed in the cavity of a standard tabletting machine and the pressure adjusted to yield a tablet which can remain intact for handling but retains its light weight.

Example 20

The following components were added to a quantity of purified water sufficient to produce a mixture with a volume of 400 ml:

| | |
|---|---|
| Mannitol | 60.0 g |
| Gelatin USP | 2.0 g |
| Gelatin Hydrolysate | 1.0 g |
| Acacia | 1.0 g |
| PVP-40 | 4.0 g |
| Sodium Bicarbonate | .15 g |
| Acetone | 120 ml |

The mixture was introduced into a Buchi model 190 spray drier with a heat setting of 9, an aspirator setting of 2, a flow rate setting of 5.5, a flow control setting of 700, and a vacuum setting of −20. Chamber temperatures were measured at approximately 5 minute consecutive intervals during the drying process. The temperatures at the flow inlet point were 145° C., 156° C., 159° C., 154C. and 157C. The temperatures at the flow outlet point (the point where the dried product exits the drying chamber to product collector) were measured as 110° C., 100° C., 104° C., 103° C., and 103° C. The product had a specific bulk volume of about 4.8 ml/g. The resulting matrix had a dissolution time of less than 20 seconds. The mixture had a ratio of the first component (unmodified gelatin) and the second component (hydrolyzed gelatin) of 2:1.

Example 21

The following components were added to a quantity of purified water sufficient to produce a mixture with a volume of 400 ml:

| | |
|---|---|
| Mannitol | 60.0 g |
| Gelatin USP | 2.0 g |
| Gelatin Hydrolysate | 1.0 g |
| PVP-40 | 6.0 g |
| Ethanol | 120 ml |

The mixture was introduced into a Buchi model 190 spray drier with a heat setting of 10, an aspirator setting of 2 (which was increased to 5 after the fourth time interval), a flow rate setting of 4.27, a flow control setting of 700, and a vacuum setting of −20. Chamber temperatures were measured at approximately 5 minute consecutive intervals during the drying process. The temperatures at the flow inlet point were 156° C., 155° C., 155° C., 154° C., and 154° C. The temperatures at the flow outlet point (the point where the dried product exits the drying chamber to product collector) were measured as 118° C., 108° C., 108° C., 109° C., 110° C., and 110° C. The product had a specific bulk volume of about 3.7 ml/g. Dissolution time of the support matrix was less than 20 seconds. The mixture had a ratio of the first component (unmodified gelatin) and the second component (hydrolyzed gelatin) of 2:1.

Example 22

The following components were added to a quantity of purified water sufficient to produce a mixture with a volume of 400 ml and a pH of 4.0:

| | |
|---|---|
| Mannitol | 60 g |
| Gelatin USP | 2.3 g |
| Gelatin Hydrolysate | 1.3 g |
| PVP-40 | 4.3 g |
| Acetone | 120 ml |

The mixture was introduced into a Buchi model 190 spray drier with a heat setting of 9, an aspirator setting of 2, a flow rate setting of 5.5, an initial flow control setting of 700, and a vacuum setting of −20. Chamber temperatures were measured at approximately 5 minute consecutive intervals during the drying process. The temperatures at the flow inlet point were 143° C., 143° C., 143° C., 143° C., and 143° C. The temperatures at the flow outlet point (the point where the dried product exits the drying chamber to product collector) were measured as 100° C., 98° C., 90° C., 91° C., and 86° C. The particulate support matrix product had a specific bulk volume of 2.8 ml/g. Dissolution time of the matrix was less than 5 seconds. The mixture had a ratio of the first component (unmodified gelatin) and the second component (hydrolyzed gelatin) of 1.8:1.

Example 23

The following components were added to a quantity of purified water sufficient to produce a mixture with a volume of 400 ml:

| | |
|---|---|
| Mannitol | 60 g |
| Gelatin USP | 2.3 g |
| Gelatin Hydrolysate | 1.3 g |
| PVP-40 | 4.3 g |
| Acetone | 120 ml |

The mixture was introduced into a Buchi model 190 spray drier with a heat setting of 9, an aspirator setting of 113 changing to 105, a flow rate setting of 4.27 changing to 8.4, an initial flow control setting of 700, and a vacuum setting of −40. Chamber temperatures were measured at approximately 5 minute consecutive intervals during the drying process. The temperatures at the flow inlet point were 147° C. initially changing to 143° C. The temperatures at the flow outlet point (the point where the dried product exits the drying chamber to product collector) were measured at 113° C. changing to 105° C. The particulate support matrix product had a specific bulk volume of 2.8 ml/g. Dissolution time of the support matrix was less than 20 seconds. The mixture had a ratio of the first component (unmodified gelatin) and the second component (hydrolyzed gelatin) of 1.8:1.

Example 24

The following components were added to a quantity of purified water sufficient to produce a mixture with a volume of 400 ml and a pH of 2.6:

| | |
|---|---|
| Mannitol | 60 g |
| Gelatin A8-275 | 1.2 g |
| Gelatin Hydrolysate | 1.0 g |
| Acacia | 0.4 g |
| Explotab ® | 0.6 g |
| PVP-40 | 0.6 g |
| Tartaric Acid | 1.8 g |
| Citric Acid | 1.8 g |
| Alginic Acid | 0.4 g |
| Ethanol | 120 ml |

The mixture was introduced into a Buchi model 190 spray drier with a heat setting of 10, an aspirator setting of 5, a flow rate setting of 4.27, an initial flow control setting of 700 (changing to 500 after the first time interval), and a vacuum setting of −20. Chamber temperatures were measured at approximately 5 minute consecutive intervals during the drying process. The temperatures at the flow inlet point were 156° C. changing to 154° C. The temperatures at the flow outlet point (the point where the dried product exits the drying chamber to product collector) were measured as 118° C. changing to 108° C. Dissolution time was less than 20 seconds. The mixture had a ratio of the first component (unmodified gelatin) and the second component (hydrolyzed gelatin) of 1.2:1.

Example 25

The following components were added to a quantity of purified water sufficient to produce a mixture with a volume of 1000 ml and a pH of 3.6:

| | |
|---|---|
| Mannitol | 20 g |
| Gelatin NF | 2.0 g |
| Gelatin Hydrolysate | 4.0 g |
| Sorbitol | 5.0 g |
| Xylitol | 5.0 g |
| Propylene Glycol | 10 drops |
| 5% HAC | q.s. |
| Sucrose | 0.66 g |
| Citric Acid | 1.0 g |
| Ethanol | 300 ml |

The mixture was introduced into a Buchi model 190 spray drier with a heat setting of 8.5, an aspirator setting of 0 changing to 1, a flow rate setting of 4.55, a flow control setting of 700, and a vacuum setting of −20. Chamber temperatures were measured at approximately 5 minute consecutive intervals during the drying process. The temperatures at the flow inlet point were 136° C., 135° C., 135° C., 135° C., and 137° C. The temperatures at the flow outlet point (the point where the dried product exits the drying chamber to product collector) were measured as 97° C., 95° C., 93° C., 90° C. and 85° C. Dissolution time was less than 20 seconds. The mixture had a ratio of the first component (unmodified gelatin) and the second component (hydrolyzed gelatin) of 1:2.

Example 26

The following components were added to a quantity of purified water sufficient to produce a mixture with a volume of 1000 ml and a pH of 3.6:

| | |
|---|---|
| Mannitol | 20.0 g |
| Gelatin NF | 1.5 g |
| Gelatin Hydrolysate | 4.0 g |
| Sorbitol | 10 g |
| Propylene Glycol | 10 drops |
| HAC | 15 drops |
| Sucrose | 0.65 g |
| Citric Acid | 1.5 g |
| Ethanol | 300 ml |

The mixture was introduced into a Buchi model 190 spray drier with a heat setting of 8.4, an aspirator setting of 0 changing to 1, a flow rate setting of 4.55, a flow control setting of 700 (changing to 680 after the first time interval), and a vacuum setting of −20. Chamber temperatures were measured at approximately 5 minute consecutive intervals during the drying process. The temperature at the flow inlet point was 135° C. The temperatures at the flow outlet point (the point where the dried product exits the drying chamber to product collector) were measured as 88° C. changing to 83° C. The particulate support matrix product had a specific bulk volume of 18.7 ml/g. Dissolution time was about 10 seconds. The mixture had a ratio of the first component (unmodified gelatin) and the second component (hydrolyzed gelatin) of 1:2.7.

Example 27

The following components were added to a quantity of purified water sufficient to produce a mixture with a volume of 1000 ml and a pH of 3.5:

| | |
|---|---|
| Mannitol | 20 g |
| Sorbitol | 5.0 g |
| Xylitol | 5.0 g |
| Gelatin NF | 1.0 g |
| Gelatin Hydrolysate | 3.0 g |
| Acetic Acid, Glacial | 15 drops |
| Propylene Glycol | 10 drops |
| Sucrose | 0.67 g |
| Citric Acid | 1.0 g |
| Ethanol | 300 ml |

The mixture was introduced into a Buchi model 190 spray drier with a heat setting of 8.2 an aspirator setting of 0, changing to 2, a flow rate setting of 3, a flow control setting of 680, and a vacuum setting of −20. Chamber temperatures were measured at approximately 5 minute consecutive intervals during the drying process. The temperature at the flow inlet point was 136° C. The temperatures at the flow outlet point (the point where the dried product exits the drying chamber to product collector) were measured as 93° C., 90° C., 88° C., 84° C., and 81° C. The particulate support matrix product had a specific bulk volume of about 1.3 ml/g. Dissolution time was 1–15 seconds. The mixture had a ratio of the first component (unmodified gelatin) and the second component (hydrolyzed gelatin) of 1:3.

Example 28

The following components were added to a quantity of purified water sufficient to produce a mixture with a volume of 100 ml.

| Sucrose | 0.65 g |
| --- | --- |
| Mannitol | 18.0 g |
| Sorbitol | 5.0 g |
| Xylitol | 5.0 g |
| Gelatin NF | 1.0 g |
| Gelatin Hydrolysate | 3.0 g |
| Citric Acid | 1.0 g |
| Explotab ® | 0.3 g |
| Propylene Glycol | 10 drops |
| 5% HAC | q.s. |
| Ethanol | 300 ml |

The mixture was introduced into a Buchi model 190 spray drier with a heat setting of 8.5, an aspirator setting of 0, changing to 2, a flow rate setting of 4.55, a flow control setting of 700, and a vacuum setting of −20. Chamber temperatures were measured at approximately 5 minute consecutive intervals during the drying process. The temperatures at the flow inlet point were 139° C. changing to 137° C. The temperatures at the flow outlet point (the point where the dried product exits the drying chamber to product collector) were measured as 91° C. changing to 87° C. Dissolution time of the product was 5–15 seconds. The mixture had a ratio of the primary component (unmodified gelatin) and the second component (hydrolyzed gelatin) of 1:3.

Example 29

The following components were added to a quantity of purified water sufficient to produce a mixture with a volume of 1000 ml and a pH of 3.9:

| Sorbitol | 11.0 g |
| --- | --- |
| Mannitol | 19.0 g |
| Gelatin NF | 1.0 g |
| Gelatin Hydrolysate | 4.0 g |
| Sucrose | 0.66 g |
| Propylene Glycol | 10 drops |
| 5% HAC | q.s. |
| Citric Acid | 1.0 g |
| Ethanol | 300 ml |

The mixture was introduced into a Buchi model 190 spray drier with a heat setting of 8.5, an aspirator setting of 0 changing to 0.5, a flow rate setting of 4, a flow control setting of 600, and a vacuum setting of −20.

Chamber temperatures were measured at approximately 5 minute consecutive intervals during the drying process. The temperatures at the flow inlet point were 138° C. changing to 133° C. The temperatures at the flow outlet point (the point where the dried product exits the drying chamber to product collector) were measured as 102° C. changing to 89° C. Dissolution time was less than 20 seconds. The mixture had a ratio of the primary component (unmodified gelatin) and the second component (hydrolyzed gelatin) of 1:4.

Example 30

The following components were added to a quantity of purified water sufficient to produce a mixture with a volume of 1000 ml and a pH of 3.5.

| Mannitol | 18.0 g |
| --- | --- |
| Sorbitol | 5.0 g |
| Xylitol | 5.0 g |
| Gelatin NF | .75 g |
| Gelatin Hydrolysate | 3.5 g |
| Explotab ® | 0.3 g |
| Citric Acid | 1.0 g |
| Polyethylene Glycol | 10 drops |

The mixture was introduced into a Buchi model 190 spray drier with a heat setting of 8.5, an aspirator setting of 0, changing to 4, a flow rate setting of 4.55, a flow control setting of 700, and a vacuum setting of −20. Chamber temperatures were measured at approximately 5 minute consecutive intervals during the drying process. The temperatures at the flow inlet point were 147° C. changing to 136° C. The temperatures at the flow outlet point (the point where the dried product exits the drying chamber to product collector) were measured as 98° C. changing to 89° C. Dissolution time was less than 20 seconds. The mixture had a ratio of the primary component (unmodified gelatin) and the second component (hydrolyzed gelatin) of 1:4.67.

Example 31

The following components were added to a quantity of purified water sufficient to produce a mixture with a volume of 1000 ml and a pH of 3.6:

| Mannitol | 18.0 g |
| --- | --- |
| Sorbitol | 5.0 g |
| Xylitol | 5.0 g |
| Sucrose | 0.65 g |
| Gelatin NF | 0.5 g |
| Gelatin Hydrolysate | 3.5 g |
| Citric Acid | 1.0 g |
| 5% HAC | 10 drops |
| Propylene Glycol | 10 drops |
| Explotab ® | 0.3 g |
| Ethanol | 300 ml |

The mixture was introduced into a Buchi model 190 spray drier with a heat setting of 8.5, an aspirator setting of 0 which changed to 1, a flow rate setting of 4.55, a flow control setting of 700, and a vacuum setting of −20. Chamber temperatures were measured at approximately 5 minute consecutive intervals during the drying process. The temperatures at the flow inlet point were 139° C. changing to 135° C. The temperatures at the flow outlet point (the point where the dried product exits the drying chamber to product collector) were measured as 98° C. changing to 88° C. The particulate support matrix product had a dissolution time of less than 20 seconds. The mixture had a ratio of the primary component (unmodified gelatin) and the second component (hydrolyzed gelatin) of 1:7.

Example 32

The following components were added to a quantity of purified water sufficient to produce a mixture with a volume of 1000 ml and a pH of 3.5:

| Mannitol | 16.0 g |
|---|---|
| Sorbitol | 7.0 g |
| Gelatin NF | 0.5 g |
| Gelatin Hydrolysate | 5.0 g |
| Citric Acid | 1.0 g |
| Sucrose | 0.65 g |
| Xylitol | 5.0 g |
| Explotab ® | 0.3 g |
| 5% HAC | q.s |
| Polyethylene Glycol | 10 drops |
| Ethanol | 300 ml |

The mixture was introduced into a Buchi model 190 spray drier with a heat setting of 8.5, an aspirator setting of 0 which changed to 1, a flow rate setting of 4.55, a flow control setting of 700, and a vacuum setting of −20. Chamber temperatures were measured at approximately 5 minute consecutive intervals during the drying process. The temperatures at the flow inlet point were 141° C changing to 132° C. The temperatures at the flow outlet point (the point where the dried product exits the drying chamber to product collector) were measured as 92° C. changing to 88° C. to 91° C. The particulate support matrix product had a dissolution time of less than 20 seconds. The mixture had a ratio of the primary component (unmodified gelatin) and the second component (hydrolyzed gelatin) of 1:10.

Example 33

The following components were added to a quantity of purified water sufficient to produce a mixture with a volume of 1000 ml and a pH of 3.5:

| Mannitol | 16.0 g |
|---|---|
| Sorbitol | 7.0 g |
| Xylitol | 5.0 g |
| Sucrose | 0.65 g |
| Gelatin NF | 0.5 g |
| Gelatin Hydrolysate | 7.0 g |
| Citric Acid | 1.0 g |
| Explotab ® | 0.3 g |
| 5% HAC | q.s |
| Polyethylene Glycol | 10 drops |
| Ethanol | 300 ml |

The mixture was introduced into a Buchi model 190 spray drier with a heat setting of 8.5, an aspirator setting of 0 changing to 1, a flow rate setting of 4.55, an initial flow control setting of 700, and a vacuum setting of −20. Chamber temperatures were measured at approximately 5 minute consecutive intervals during the drying process. The temperature at the flow inlet point was 136° C. to 138° C. The temperatures at the flow outlet point (the point where the dried product exits the drying chamber to product collector) were measured as 99° C. to 90° C. The particulate support matrix product had a dissolution time of less than 20 seconds. The mixture had a ratio of the primary component (unmodified gelatin) and the second component (hydrolyzed gelatin) of 1:14.

Example 34

The following components were added to a quantity of purified water sufficient to produce a mixture with a volume of 500 ml:

| Mannitol | 10.0 g |
|---|---|
| Sorbitol | 2.5 g |
| Xylitol | 2.5 g |
| Sucrose | 0.325 g |
| Gelatin | 0.75 g |
| Gelatin Hydrolysate | 2.0 g |
| Acetic Acid | 8 drops |
| Tartaric Acid | 0.75 g |
| Propylene Glycol | 5 drops |
| Flavoring | (see below) |
| Ethanol | 150 ml |

The mixture was introduced into a Buchi model 190 spray drier with a heat setting of 8, an aspirator setting of 0.5, a flow rate setting of 4.5, an initial flow control setting of 600, and a vacuum setting of −20. The temperature at the flow inlet point was 133° C. The temperatures at the flow outlet point (the point where the dried product exits the drying chamber to product collector) was measured as 89° C. The particulate support matrix product had a dissolution time of less than 20 seconds. The mixture had a ratio of the primary component (unmodified gelatin) and the second component (hydrolyzed gelatin) of 1:2.67.

Separate formulations were made with each of the flavorings and quantities thereof listed below. Each formulation produced a flavored support matrix having the corresponding density. Densities were calculated based on the volume associated with 18.825 gm of support matrix.

| Flavoring | Quantity Used | Powder Volume | Density |
|---|---|---|---|
| Anise oil, NF | 0.5 mL | 160 mL | 0.118 |
| Banana extract (Food grade) | 10 mL | 140 mL | 0.134 |
| Grape, Artificial | 1 mL | 180 mL | 0.105 |
|  | 3 mL | 170 mL | 0.111 |
| Lemon Oil, NF | 0.25 mL | 140 mL | 0.134 |
| Menthol, USP | 1 g | 100 mL | 0.188 |
| Methyl salicylate, Reagent | 1 mL | 170 mL | 0.111 |
|  | 3 mL | 160 mL | 0.118 |
| Orange oil, USP | 0.2 mL | 50 mL | 0.376 |
|  | 1 mL | 45 mL | 0.418 |
| Orange extract (Food grade) | 3 mL | 150 mL | 0.126 |
| Peppermint oil, Laboratory grade | 0.5 mL | 60 mL | 0.314 |
| Strawberry (Imitation Extract) | 3 mL | 160 mL | 0.118 |

Example 35

The following are examples of coating compositions referred to above which can be used to coat the formed tablets. Coating agents can be applied by dropping, by spraying or by passing the tablet through an environment saturated with the coating agent.

| I. | PVP-40 | 10% |
|---|---|---|
|  | PEG 1450 | 10% |
|  | Chloroform | 80% |
| II. | PVP-10 | 100 mg |
|  | Absolute Alcohol | 5 ml |
|  | Ether | 18 ml |

-continued

|      |              |                              |
|------|--------------|------------------------------|
| III. | PEG 1450     | 170 mg                       |
|      | Absolute Alcohol | 7 ml                     |
|      | Ether        | 14 ml                        |
| IV.  | PVP-10       | 0.5%                         |
|      | PVP-40       | 0.5%                         |
|      | PEG 1540     | 1.0%                         |
|      | Chloroform   | 98%                          |
| V.   | PVP-10       | 1.0%                         |
|      | PVP-40       | 1.0%                         |
|      | PEG 1450     | 1%                           |
|      | PEG 3350     | 1%                           |
|      | Chloroform   | 96%                          |
| VI   | PEG 1450     | 5%                           |
|      | PEG 3350     | 5%                           |
|      | Chloroform   | 90%                          |
| VII. | PEG 1450     | 5%                           |
|      | PEG 3350     | 5%                           |
|      | PVP 10/PVP40 | 0.1–0.5% (one or the other)  |
|      | Chloroform   | 89.5%                        |
| VIII.| PEG 3350     | 20. g                        |
|      | Acetone to make | 100 ml                    |

Acetone may be substituted for chloroform or ether in the above formulations. Formulas VI and VIII are preferred coating compositions due to their tendency to leave tablet volume unaffected. Solvents other than ether, alcohol and chloroform may be used. These include ethyl acetate and other types of organic solvents.

As noted above, forming a coating on the tablet by a sintering method is also a preferred coating method. Examples 36–37 describe processes for making tablets wherein a sintering method is used to form a coating on the tablet.

Example 36

A. Product A

1. Preparation of sintered placebo tablets:

a) Combine 170 mg of the support matrix (60 mesh sieve) with 170 mg of a fine powder mixture of 50% PEG-3350, 7.5% PEG-4000 and 32.5% PEG-6000.

b) Blend thoroughly and then compress into tablets. Heat tablets at 90° C. for ten minutes in the oven. Remove.

B. Product B

1. Preparation of Sintered tablets of chlorpheniramine maleate a) Combine chlorpheniramine maleate 4 mg, L-lysine monohydrochloride 7.5 mg, Urea powder (325 mesh) 0.5 mg, DL-glutamic acid 0.25 mg, Saccharin Sodium 0.75 mg, and 166 mg of the support matrix with 160 mg of a fine powder mixture of 50% PEG-3350, 17.5% PEG-4000 and 32.5% PEG-6000.

b) Blend completely, and then compress into tablets. Heat at 90° C. for ten minutes in the oven.

Example 37

1. Preparation of sintered tablets of chlorpheniramine maleate (alternative version):

a) Chlorpheniramine maleate 4 mg, L-lysine monohydrochloride 7.5 mg, Urea (fine powder) 0.5 mg, DL-glutamic acid 0.25 mg, Saccharin Sodium 0.75 mg, support matrix powder 166 mg and PEG-4000 powder (325 mesh) 166 mg were combined.

b) The uniformly mixed powders were moistened with 15 drops of 10% propylene glycol in isopropyl alcohol to ensure that active drug was uniformly adsorbed onto the network structure of support matrix to meet uniformity of dosage units. The slightly moistened mixture of powders was placed in the oven at 40° C. for 15 minutes to remove organic solvent and was finally compressed into tablets.

c) The tablets thus obtained were placed in the oven at 90° C. for 10 minutes and then stored in a desiccator and packaged.

Changes may be made in the construction and the operation of the various components, elements and assemblies described herein or in the steps or the sequence of steps of the methods described herein without departing from the spirit and scope of the invention as defined in the following claims.

What is claimed is:

1. A rapidly dissolving pharmaceutical dosage form produced by the process comprising:

providing a quantity of a particulate support matrix produced by the process of providing an aqueous composition comprising:

an aqueous medium, a support agent comprising a non-hydrolyzed gelatin component having a predetermined net charge, a hydrolyzed gelatin component having a predetermined net charge of the same sign as the non-hydrolyzed gelatin component, and a bulking agent and wherein the hydrolyzed gelatin component has a solubility in aqueous solution greater than that of the non-hydrolyzed component, and a volatilizing agent; and introducing the aqueous composition as droplets into a drying chamber heated to a temperature sufficient to cause evaporation of substantially all of the aqueous medium and volatilizing agent from the droplets leaving the support agent in a dried particulate form comprising the particulate support matrix;

combining the quantity of the particulate support matrix with a quantity of a pharmaceutical ingredient forming a dosage mixture; and forming the dosage mixture into a dosage form which when introduced into an aqueous environment is substantially completely disintegrable within less than about 20 seconds.

2. The process of claim 1 wherein the non-hydrolyzed gelatin component and the hydrolyzed gelatin component both have a net positive charge or a net negative charge.

3. The process of claim 1 comprising the additional step of forming a layer on the external surface of the dosage form.

4. The process of claim 3 wherein the layer is formed by a sintering process.

5. The process of claim 1 wherein the particulate support matrix further comprises an effervescing agent.

6. The process of claim 1 wherein the particulate support matrix further comprises a binding agent.

7. The process of claim 1 wherein the particulate support matrix further comprises a flavoring agent.

8. The process of claim 1 wherein the dosage form is substantially completely disintegrable within less than about 10 seconds when introduced into an aqueous environment.

9. The process of claim 1 wherein the dosage form is substantially completely disintegrable within from about 1 second to about 6 seconds when introduced into an aqueous environment.

10. The process of claim 1 wherein the non-hydrolyzed gelatin component and the hydrolyzed gelatin component together comprise from about 2% to 35% of the particulate support matrix and the bulking agent comprises about 45% to 97% of the particulate support matrix.

11. A rapidly dissolving pharmaceutical dosage form produced by the process comprising:

provding a quantity of a particulate support matrix produced by the process of providing an aqueous composition comprising:
an aqueous medium,
a support agent comprising a first gelatin component having a predetermined net charge, a second gelatin component having a predetermined net charge of the same sign as the first gelatin component, and a bulking agent and wherein the second gelatin component has a solubility in aqueous solution greater than that of the first gelatin component, and
a volatilizing agent; and
introducing the aqueous composition as droplets into a drying chamber heated to a temperature sufficient to cause evaporation of substantially all of the aqueous medium and volatilizing agent from the droplets leaving the support agent in a dried particulate form comprising the particulate support matrix;

combining the quantity of the particulate support matrix with a quantity of a pharmaceutical ingredient forming a dosage mixture; and forming the dosage mixture into a dosage form which when introduced into an aqueous environment is substantially completely disintegrable within less than about 20 seconds.

12. The process of claim 11 wherein the first gelatin component comprises a first hydrolyzed gelatin and the second gelatin component comprises a second hydrolyzed gelatin, the second hydrolyzed gelatin having a molecular weight less than the molecular weight of the first hydrolyzed gelatin.

13. The process of claim 11 wherein the first gelatin component and the second gelatin component both have a net positive charge or a net negative charge.

14. The process of claim 11 comprising the additional step of forming a layer on the external surface of the dosage form.

15. The process of claim 14 wherein the layer is formed by a sintering process.

16. The process of claim 11 wherein the particulate support matrix further comprises an effervescing agent.

17. The process of claim 11 wherein the particulate support matrix further comprises a binding agent.

18. The process of claim 11 wherein the particulate support matrix further comprises a flavoring agent.

19. The process of claim 11 wherein the dosage form is substantially completely disintegrable within less than about 10 seconds when introduced into an aqueous environment.

20. The process of claim 11 wherein the dosage form is substantially completely disintegrable within from about 1 second to about 6 seconds when introduced into an aqueous environment.

21. The process of claim 11 wherein the first gelatin component and the second gelatin component together comprise from about 2% to 35% of the particular support matrix and the bulking agent comprises about 45% to 97% the particulate support matrix.

22. A rapidly dissolving pharmaceutical dosage form produced by the process comprising:

providing a quantity of a particulate support matrix produced by the process of providing an aqueous composition comprising:
an aqueous medium,
a support agent comprising a first gelatin component having a predetermined net charge, a second gelatin component having a predetermined net charge of the same sign as the first gelatin component, and a bulking agent and wherein the second gelatin component has a solubility in aqueous solution greater than that of the first gelatin component, and
a volatilizing agent; and
introducing the aqueous composition as droplets into a drying chamber heated to a temperature sufficient to evaporate substantially all of the aqueous medium and volatilizing agent from the droplets leaving the support agent in a dried particulate form comprising the particulate support matrix;

combining the quantity of the particulate support matrix with a quantity of a pharmaceutical ingredient forming a dosage mixture; and forming the dosage mixture into a dosage form and sintering the dosage form forming a surface coating thereon and wherein the dosage form is substantially disintegrable within less than about 20 seconds when introduced into an aqueous environment.

23. A rapidly dissolving pharmaceutical dosage form produced by the process comprising:

providing a quantity of a particulate support matrix produced by the process of providing an aqueous composition comprising:
an aqueous medium,
a support agent comprising a non-hydrolyzed gelatin component having a predetermined net charge, a hydrolyzed gelatin component having a predetermined net charge of the same sign as the non-hydrolyzed gelatin component, and a bulking agent and wherein the hydrolyzed gelatin component has a solubility in aqueous solution greater than that of the non-hydrolyzed component, and
a volatilizing agent; and
introducing the aqueous composition as droplets into a drying chamber heated to a temperature sufficient to cause evaporation of substantially all of the aqueous medium and volatilizing agent from the droplets leaving the support agent in a dried particulate form comprising the particulate support matrix;

combining the quantity of the particulate support matrix with a quantity of a pharmaceutical ingredient forming a dosage mixture; and forming the dosage mixture into a dosage form and sintering the dosage form forming a surface coating thereon and wherein the dosage form is substantially disintegrable within less than about 20 seconds when introduced into an aqueous environment.

* * * * *

UNITED STATES PATENT AND TRADEMARK OFFICE
CERTIFICATE OF CORRECTION

PATENT NO.    :   6,066,337
DATED         :   May 23, 2000
INVENTOR(S)   :   Loyd V. ALLEN et al.

It is certified that error appears in the above-identified patent and that said Letters Patent is hereby corrected as shown below:

Col. 2:     line 17, delete "pre-versus" and substitute --pre- versus-- therefor;

Col. 9:     line 40, delete "such a" and substitute --such as-- therefor;

Col. 14:    line 43, delete "Gelatin 275" and substitute --Gelatin G8-275-- therefor;

line 53, delete "Gelatin 275" and substitute --Gelatin G8-275-- therefor; and

Col. 17:    line 44, delete "Hyarolysate" and substitute therefor --Hydrolysate-- therefor.

Signed and Sealed this

Seventeenth Day of April, 2001

Attest:

NICHOLAS P. GODICI

Attesting Officer      Acting Director of the United States Patent and Trademark Office